US009284254B2

(12) United States Patent
Nadal et al.

(10) Patent No.: US 9,284,254 B2
(45) Date of Patent: Mar. 15, 2016

(54) PROCESS FOR THE CONTINUOUS MANUFACTURE OF ARYL ALKYL CARBONATE AND/OR DIARYL CARBONATE USING VAPOR RECOMPRESSION (71) Applicant: SABIC Innovative Plastics IP B.V., Bergen op Zoom (NL)

(72) Inventors: Sergio Ferrer Nadal, Granada (ES); Ignacio Vic Fernandez, Murcia (ES); Jose Antonio Caballero, Alicante (ES); Juan Javaloyes Anton, Alicante (ES)

(73) Assignee: SABIC GLOBAL TECHNOLOGIES B.V. (NL)

( * ) Notice: Subject to any disclaimer, the term of this patent is extended or adjusted under 35 U.S.C. 154(b) by 259 days.

(21) Appl. No.: 14/031,836

(22) Filed: Sep. 19, 2013

(65) Prior Publication Data
US 2014/0081039 A1    Mar. 20, 2014

(30) Foreign Application Priority Data
Sep. 20, 2012    (EP) .................................... 12382368

(51) Int. Cl.
C07C 68/06    (2006.01)
C07C 68/08    (2006.01)

(52) U.S. Cl.
CPC ............... C07C 68/065 (2013.01); C07C 68/06 (2013.01); C07C 68/08 (2013.01)

(58) Field of Classification Search
None
See application file for complete search history.

(56) References Cited

U.S. PATENT DOCUMENTS

| 3,642,858 | A  | 2/1972  | Frevel et al. |
| 3,803,201 | A  | 4/1974  | Gilpin et al. |
| 4,181,676 | A  | 1/1980  | Buysch et al. |
| 4,252,737 | A  | 2/1981  | Krimm et al. |
| 4,330,665 | A  | 5/1982  | Krimm et al. |
| 4,552,704 | A  | 11/1985 | Mark |
| 4,554,110 | A  | 11/1985 | Mark |
| 5,872,275 | A  | 2/1999  | Komiya et al. |
| 6,835,858 | B1 | 12/2004 | De Jonge et al. |
| 7,067,610 | B2 | 6/2006  | Vaporciyan |
| 7,629,485 | B2 | 12/2009 | Miyake |
| 7,732,629 | B2 | 6/2010  | Van Der Heide et al. |
| 8,003,817 | B2 | 8/2011  | Dux et al. |
| 8,039,659 | B2 | 10/2011 | Dux et al. |
| 8,110,698 | B2 | 2/2012  | Ryu |
| 8,138,367 | B2 | 3/2012  | Miyake |
| 2008/0255336 | A1 | 10/2008 | Nisbet et al. |
| 2009/0023884 | A1 | 1/2009  | Vaporciyan |
| 2009/0131706 | A1 | 5/2009  | Vaporciyan |
| 2009/0209724 | A1 | 8/2009  | Fukuoka et al. |
| 2010/0261928 | A1 | 10/2010 | Dux et al. |
| 2011/0152558 | A1 | 6/2011  | Huang et al. |
| 2011/0213173 | A1 | 9/2011  | Van Der Heide et al. |
| 2011/0245527 | A1 | 10/2011 | Ooms et al. |
| 2012/0172573 | A1 | 7/2012  | Kim et al. |

FOREIGN PATENT DOCUMENTS

| BE | 1006062    | A3 | 5/1994 |
| EP | 0000879    | A1 | 7/1979 |
| EP | 0338760    | A2 | 10/1989 |
| JP | 54125617   | A  | 9/1979 |
| JP | 57176932   |    | 10/1982 |
| JP | 61172852   | A  | 8/1986 |
| JP | 200193560  | A  | 4/2001 |
| WO | 2010063694 | A1 | 6/2010 |
| WO | 2011018448 | A1 | 2/2011 |
| WO | 2011058168 | A1 | 5/2011 |
| WO | 2011067263 | A1 | 6/2011 |
| WO | 2011105442 | A1 | 9/2011 |
| WO | 2012076532 | A1 | 6/2012 |
| WO | 2013007597 | A1 | 1/2013 |
| WO | 2013007601 | A1 | 1/2013 |

OTHER PUBLICATIONS

JP02186186 English Abstract; Date of Publication Jul. 20, 1990; 1 page.
BE1006062 English Abstract.
EP0000879 A1; English Abstract; Date of Publication Mar. 7, 1979; 1 page.
European Search Report for European Patent Application 12382368. 4-2103; Date of Issue Jan. 30, 2013; 8 pages.
JP2001093560 English Abstract; Date of Publication Apr. 6, 2001; 8 pages.
JP54125617 English Abstract; Date of Publication Sep. 29, 1979; 1 page.
JP57176932 English Abstract; Date of Publication Oct. 30, 1982; 1 page.
JP61172852 English Abstract; Date of Publication Aug. 4, 1986; 1 page.
International Search Report for International Application No. PCT/IB2012/057804; International Filing Date Dec. 28, 2012; Date of Mailing Mar. 12, 2013; 5 pages.
Written Opinion of the International Search Report for International Application No. PCT/IB2012/057804; International Filing Date Dec. 28, 2012; Date of Mailing Mar. 12, 2013; 8 pages.

Primary Examiner — Michael Barker
Assistant Examiner — Po-Chih Chen
(74) Attorney, Agent, or Firm — Cantor Colburn LLP (57) ABSTRACT In an embodiment, a process for preparing an alkyl aryl carbonate and a diaryl carbonate, comprising: reacting a dialkyl carbonate and an aromatic hydroxy compound in a production column to form the alkyl aryl carbonate and the diaryl carbonate; directing a bottom stream of the production column to a reboiler, wherein the bottom stream comprises the alkyl aryl carbonate and the diaryl carbonate; heating the bottom stream in the reboiler with heat from an overhead stream of the production column to result in a heated bottom stream; directing a first portion of the heated bottom stream back into the production column, wherein the first portion comprises an aromatic hydroxy compound; and collecting the diaryl carbonate and the alkyl aryl carbonate from a second portion of the heated bottom stream.

17 Claims, 2 Drawing Sheets

PROCESS FOR THE CONTINUOUS MANUFACTURE OF ARYL ALKYL CARBONATE AND/OR DIARYL CARBONATE USING VAPOR RECOMPRESSION

CROSS REFERENCE TO RELATED APPLICATIONS

The present application claims priority to European Application Ser. No. 12382368.4, filed Sep. 20, 2012, the contents of which are incorporated herein in their entirety by reference.

BACKGROUND

The preparation of aromatic and aliphatic-aromatic carbonic acid esters (carbonates) by transesterification starting from aliphatic carbonic acid esters and aromatic hydroxy compounds is known in principle. For example, a non-phosgene route to synthesize the diaryl carbonate of diphenyl carbonate (DPC) can be achieved through the transesterification of dimethyl carbonate (DMC) and phenol to produce phenyl methyl carbonate (PMC) as shown in Reaction (1), wherein the equilibrium constant at the range of operating temperatures can be on the order of $10^{-3}$, followed by the subsequent disproportionation of PMC to produce diphenyl carbonate (DPC) as shown in Reaction (2), wherein the additional formation of small amounts of an alkyl aryl ether (anisole) as the main reaction byproduct.

The production of diaryl carbonate in this manner is a highly energy intensive process due to the large amount of thermal energy needed in the first step, preparing the alkyl aryl carbonate. This energy is obtained from, for example, an external heating medium such as high-pressure steam. This large amount of thermal energy is used to overcome the unfavorable thermodynamics of the reaction scheme above. Without the introduction of this thermal energy, the reaction conversions are low. In addition to the large amount of thermal energy, a large excess amount of one of the reactants can be used to displace the equilibrium and to strip the more volatile alkyl alcohol (methanol) produced in Reaction (1). When such an excess of one of the reactants is used, the production process can require an extra recovery and recycle step.

A more efficient process of producing diaryl carbonate that could accomplish one or both of reducing the amount of thermal energy needed to facilitate the production of diaryl carbonate and reducing the amount of unreacted components and/or intermediate unreacted components that need to be recovered and recycled is desirable. Increasing the efficiency of the process could result in an increase its economic feasibility and/or reduce flue gas emissions directly associated with the energetic consumption.

SUMMARY

Disclosed herein are processes for preparing an alkyl aryl carbonate and a diaryl carbonate.

In an embodiment, a process for preparing an alkyl aryl carbonate and a diaryl carbonate, comprising: reacting a dialkyl carbonate and an aromatic hydroxy compound in a production column 200,300 to form the alkyl aryl carbonate and the diaryl carbonate; directing a bottom stream of the production column to a reboiler 205,305, wherein the bottom stream comprises the alkyl aryl carbonate and the diaryl carbonate; heating the bottom stream in the reboiler 205,305 with heat from an overhead stream of the production column 200,300 to result in a heated bottom stream; directing a first portion of the heated bottom stream back into the production column 200,300, wherein the first portion comprises the aromatic hydroxyl compound; and collecting the diaryl carbonate and the alkyl aryl carbonate from a second portion of the heated bottom stream.

The above described and other features are exemplified by the following figures and detailed description.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

DETAILED DESCRIPTION

The production of diaryl carbonate via the reaction of a dialkyl carbonate and an aromatic hydroxy compound is a highly energy intensive process due to the large amount of thermal energy that needs to be input to the system by for example an external heating medium. In developing a more efficient process of producing diaryl carbonate, the Applicants surprisingly discovered that they could employ a mechanical vapor recompression process (also referred to as a vapor recompression cycle or just as vapor recompression) where the latent heat of condensation of the overhead stream of a production column is used to heat the bottom stream of the production column. The successful employment of vapor recompression in the production of diaryl carbonate was surprising as vapor recompression is generally not recommended for columns where there are big differences in temperature between the condenser and the reboiler, wherein even a temperature difference of 20° C. is considered an excessive temperature difference. Considering a typical production column for the diaryl carbonate of diphenyl carbonate, the bottom stream is generally at a temperature of 180 to 260° C., specifically 200 to 250° C., and more specifically 210 to 240° C. and the overhead stream is generally at a temperature of 140 to 230° C., specifically 160 to 200° C.; wherein the temperature difference is greater than or equal to 10° C., specifically, greater than or equal to 20° C. The Applicants further surprisingly found that by employing a vapor recompression cycle the cooling duty could be reduced by greater than 35% and in some instances by greater than 73%, potentially equating to large economic saving.

Diaryl Carbonate

The diaryl carbonate that can be prepared by the present method can have the formula (I)

(I)

wherein n is an integer 1 to 3 and each $R_2$ is independently linear or branched, optionally substituted $C_{1-34}$ alkyl, specifically $C_{1-6}$ alkyl, more specifically $C_{1-4}$ alkyl; $C_{1-34}$ alkoxy, specifically $C_{1-6}$ alkoxy, more specifically $C_{1-4}$ alkoxy; $C_{5-34}$ cycloalkyl; $C_{7-34}$ alkylaryl; $C_{6-34}$ aryl; or a halogen radical, specifically a chlorine radical. $R_2$ can also represent —COO—R', wherein R' can be H; optionally branched $C_{1-34}$ alkyl, specifically $C_{1-6}$ alkyl, more specifically $C_{1-4}$ alkyl; $C_{1-34}$ alkoxy, specifically $C_{1-16}$ alkoxy, specifically $C_{1-4}$ alkoxy; $C_{5-34}$ cycloalkyl; $C_{7-34}$ alkylaryl; or $C_{6-34}$ aryl.

The diaryl carbonate of the general formula (I) can comprise diphenyl carbonate, methylphenyl-phenyl carbonates and di-(methylphenyl) carbonates (wherein the methyl group can be in any desired position on the phenyl rings), dimethylphenyl-phenyl carbonates and di-(dimethylphenyl) carbonates (wherein the methyl groups can be in any desired position on the phenyl rings), chlorophenyl-phenyl carbonates and di-(chlorophenyl) carbonates (wherein the methyl group can be in any desired position on the phenyl rings), 4-ethylphenyl-phenyl carbonate, di-(4-ethylphenyl)carbonate, 4-n-propylphenyl-phenyl carbonate, di-(4-n-propylphenyl)carbonate, 4-isopropylphenyl-phenyl carbonate, di-(4-isopropylphenyl) carbonate, 4-n-butylphenyl-phenyl carbonate, di-(4-n-butylphenyl)carbonate, 4-isobutylphenyl-phenyl carbonate, di-(4-isobutylphenyl)carbonate, 4-tert-butylphenyl-phenyl carbonate, di-(4-tert-butylphenyl)carbonate, 4-n-pentylphenyl-phenyl carbonate, di-(4-npentylphenyl)carbonate, 4-n-hexylphenyl-phenyl carbonate, di-(4-n-hexylphenyl)carbonate, 4-isooctylphenyl-phenyl carbonate, di-(4-isooctylphenyl) carbonate, 4-n-nonylphenyl-phenyl carbonate, di-(4-n-nonyl-phenyl)carbonate, 4-cyclohexylphenyl-phenyl carbonate, di-(4-cyclohexylphenyl)carbonate, 4-(1-methyl-1-phenylethyl)-phenyl-phenyl carbonate, di-[4-(1-methyl-1-phenylethyl)-phenyl]carbonate, biphenyl-4-yl-phenyl carbonate, di-(biphenyl-4-yl)carbonate, (1-naphthyl)-phenyl carbonate, (2-naphthyl)-phenyl carbonate, di-(1-naphthyl)carbonate, di-(2-naphthyl)carbonate, 4-(1-naphthyl)-phenyl-phenyl carbonate, 4-(2-naphthyl)-phenyl-phenyl carbonate, di-[4-(1-naphthyl))-phenyl]carbonate, di-[4-(2-naphthyl)phenyl]carbonate, 4-phenoxyphenyl-phenyl carbonate, di-(4-phenoxyphenyl)carbonate, 3-pentadecylphenyl-phenyl carbonate, di-(3-pentadecylphenyl) carbonate, 4-tritylphenyl-phenyl carbonate, di-(4-tritylphenyl)carbonate, methyl salicylate-phenyl carbonate, di-(methyl salicylate) carbonate, ethyl salicylate-phenyl carbonate, di-(ethyl salicylate) carbonate, n-propyl salicylate-phenyl carbonate, di-(n-propyl salicylate) carbonate, isopropyl salicylate-phenyl carbonate, di-(isopropyl salicylate) carbonate, n-butyl salicylate-phenyl carbonate, di-(n-butyl salicylate) carbonate, isobutyl salicylate-phenyl carbonate, di-(isobutyl salicylate) carbonate, tert-butyl salicylate-phenyl carbonate, di-(tert-butyl salicylate) carbonate, di-(phenyl salicylate)-carbonate, di-(benzyl salicylate) carbonate, and combinations comprising one or more of the foregoing. The diaryl carbonate can be diphenyl carbonate.

The aryl alkyl carbonate can be an aryl alkyl carbonate of the formula (II)

(II)

wherein n and $R_2$ are defined as above for formula (I) and $R_1$ is linear or branched, optionally substituted $C_{1-34}$ alkyl, specifically $C_{1-6}$ alkyl, more specifically $C_{1-4}$ alkyl. The $C_{1-4}$ alkyl can comprise methyl, ethyl, n-propyl, isopropyl, n-butyl, sec-butyl, tert-butyl, or a combination comprising of one or more of the foregoing. The $C_{1-6}$ alkyl can comprise n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, or a combination comprising of one or more of the foregoing. The $C_1$-$C_{34}$-alkyl can comprise n-heptyl, n-octyl, pinacyl, adamantyl, an isomeric menthyl, n-nonyl, n-decyl, n-dodecyl, n-tridecyl, n-tetradecyl, n-hexadecyl, or n-octadecyl, or a combination comprising of one or more of the foregoing. The same applies for the corresponding alkyl radical in, for example, aralkyl or alkylaryl radicals.

Alkylene radicals in the corresponding hydroxyalkyl or aralkyl or alkylaryl radicals represent, for example, the alkylene radicals corresponding to the above alkyl radicals. Aryl represents a carbocyclic aromatic radical having from 6 to 34 skeletal carbon atoms. The same applies for the aromatic part of an arylalkyl radical, also referred to as an aralkyl radical, as well as for aryl constituents of more complex groups, such as, for example, arylcarbonyl radicals. Arylalkyl and aralkyl, each independently of the other, denote a straight-chained, cyclic, branched or unbranched alkyl radical according to the above definition which can be mono-substituted, poly-substituted, or completely substituted by aryl radicals according to the above definition.

The diaryl carbonate and/or aryl alkyl carbonate can be prepared by reacting a dialkyl carbonate and an aromatic hydroxy compound. Specifically the aromatic hydroxy compound and the dialkyl carbonate can be added in a molar ratio of 1:0.1 to 1:10, specifically 1:0.2 to 1:5, more specifically 1:0.5 to 1:3. The indicated molar ratio does not take into account any recycled components that may be added back to the production column.

Dialkyl Carbonate

The dialkyl carbonate can comprise the dialkyl carbonate of the formula (III)

(III)

wherein each $R_1$ independently is defined as above in formula (II).

The dialkyl carbonates can comprise dimethyl carbonate, diethyl carbonate, dipropyl carbonate (e.g., di(n-propyl)carbonate, and/or di(isopropyl)carbonate), dibutyl carbonate (e.g., di(n-butyl)carbonate, di(sec-butyl)carbonate, and/or di(tert-butyl) carbonate), dihexyl carbonate, or a combination comprising one or more of the foregoing.

Aromatic Hydroxy Compound

The aromatic hydroxy compound can comprise an aromatic hydroxy compound of the formula (IV)

(IV)

wherein n and $R_2$ are defined as above in formula (I).

The aromatic hydroxy compound can comprise phenol, o-, m- or p-cresol, dimethylphenol (wherein the methyl groups can be in any desired position on the phenol ring), for example 2,4-, 2,6- or 3,4-dimethylphenol, o-, m- or p-chlorophenol, o-, m- or p-ethylphenol, o-, m- or p-n-propylphenol), 4-isopropylphenol, 4-n-butylphenol, 4-isobutylphenol, 4-tert-butylphenol, 4-n-pentylphenol, 4-n-hexylphenol, 4-isooctylphenol, 4-n-nonylphenol, o-, m- or p-methoxyphenol, 4-cyclohexylphenol, 4-(1-methyl-1-phenylethyl)-phenol, biphenyl-4-ol, 1-naphthol, 2-1-naphthol, 4-(1-naphthyl)phenol, 4-(2-naphthyl)phenol, 4-phenoxyphenol, 3-pentadecylphenol, 4-tritylphenol, methylsalicylic acid, ethylsalicylic acid, n-propylsalicyclic acid, isopropyl-salicylic acid, n-butylsalicylic acid, isobutylsalicylic acid, tert-butylsalicylic acid, phenylsalicylic acid, benzylsalicylic acid, or a combination comprising one or more of the foregoing.

The aromatic hydroxy compound can comprise phenol, 4-tert-butylphenol, biphenyl-4-ol, 4-(1-methyl-1-phenylethyl)-phenol, or a combination comprising one or more of the foregoing.

Catalyst

A catalyst, that can be a transesterification catalyst, can be used to facilitate the reaction between the dialkyl carbonate and the aromatic hydroxy compound. The catalyst can be a homogeneous catalyst or a heterogeneous catalyst, wherein a heterogeneous catalyst comprises two or more catalysts. The catalyst can comprise hydrides, oxides, hydroxides, alcoholates, amides and other salts of alkali and alkaline earth metals, such as of lithium, sodium, potassium, rubidium, caesium, magnesium and calcium, specifically lithium, sodium, potassium, magnesium, calcium, or a combination comprising one or more of the foregoing. Salts of the alkali and alkaline earth metals can also be salts of organic or inorganic acids, such as of acetic acid, propionic acid, butyric acid, benzoic acid, stearic acid, carbonic acid (carbonates or hydrogen carbonates), phosphoric acid, hydrocyanic acid, thiocyanic acid, boric acid, cinnamic acid, $C_{1-4}$-stannonic acids, antimonic acid, or a combination comprising one or more of the foregoing. Suitable compounds of the alkali and alkaline earth metals can be the oxides, hydroxides, alcoholates, acetates, propionates, benzoates, carbonates, and hydrogen carbonates. The mentioned alkali or alkaline earth metal compounds can be used in amounts of 0.001 to 2 wt %, specifically 0.005 to 0.9 wt %, and more specifically 0.01 to 0.5 wt %, based on the weight of the reaction mixture to be reacted.

Further catalysts which can be used are metal compounds such as $AlX_3$, $TiX_3$, $UX_4$, $TiX_4$, $VOX_3$, $VX_5$, $ZnX_2$, $FeX_3$, $PbX_2$ and $SnX_4$, wherein X represents halogen, acetoxy, alkoxy, aryloxy radicals, or a combination comprising one or more of the foregoing. The metal compound of $AlX_3$, $TiX_4$, $PbX_2$, and $SnX_4$ can comprise titanium tetrachloride, titanium tetramethoxide, titanium tetraphenoxide, titanium tetraethoxide, titanium tetraisopropylate, titanium tetradodecylate, tin tetraisooctylate and aluminium triisopropylate. The mentioned metal compounds can be used in an amount of 0.001 to 15 wt %, more specifically 0.005 to 5 wt %, and even more specifically 0.01 to 5 wt %, based on the weight of the reaction mixture to be reacted.

Further catalysts which can be used can be organotin compounds of the general formula $(R^{11})_{4-x}$—$Sn(Y)_x$, wherein Y represents a radical $OCOR^{12}$, OH, or OR, wherein $R^{12}$ represents $C_{1-12}$ alkyl, $C_{6-12}$ aryl or $C_{7-13}$ alkylaryl, $R^{11}$ independently of $R^{12}$ has the meaning of $R^{12}$ and x represents an integer 1 to 3; dialkyltin compounds having from 1 to 12 carbon atoms in the alkyl radical; or bis-(trialkyltin) compounds, for example trimethyltin acetate, triethyltin benzoate, tributyltin acetate, triphenyltin acetate, dibutyltin diacetate, dibutyltin dilaurate, dioctyltin dilaurate, dibutyltin adipinate, dibutyldimethoxytin, dimethyltin glycolate, dibutyldiethoxytin, triethyltin hydroxide, hexaethylstannoxane, hexabutylstannoxane, dibutyltin oxide, dioctyltin oxide, butyltin triisooctylate, octyltin triisooctylate, butylstannonic acid, octylstannonic acid, or a combination comprising one or more of the foregoing. The organotin compound can be used in an amount of 0.001 to 20 wt %. The organotin compound can comprise polymeric tin compounds of the formula -[—$RR^{11}Sn$—O—]-, in which R and $R^{11}$ independently of one another have the meaning given above for $R^{12}$, for example poly[oxy(dibutylstannylene)], poly [oxy(dioctyl stannylene)], poly[oxy(butylphenyl stannylene)], and poly [oxy(diphenylstannylene)], polymeric hydroxystannoxanes of the formula -[—$RSn(OH)$—O—]-, for example poly(ethylhydroxystannoxane), poly(butylhydroxystannoxane), poly (octylhydroxysnoxane), poly(undecylhydroxystannoxane), and poly(dodecylhydroxystannoxanes), or a combination comprising one or more of the foregoing. The polymeric tin compounds can be used in an amount of 0.001 to 20 wt %, specifically 0.005 to 5 wt %, based on dialkyl carbonate. Further tin compounds, which can be used are Sn(II) oxides of the general formula X—$R^{13}Sn$—O—$R^{13}Sn$—Y, wherein X and Y independently of one another represent OH, SCN, $OR^{14}$, $OCOR^{14}$ or halogen and $R^{13}$ represents alkyl, aryl, wherein $R^{14}$ has the meaning given above for $R^{12}$.

Further catalysts are lead compounds, optionally together with triorgano-phosphanes, a chelate compound or an alkali metal halide, for example $Pb(OH)_2 \cdot 2PbCO_3$, $Pb(OCO-CH_3)_2$, $Pb(OCO-CH_3)_2 \cdot 2LiCl$, $Pb(OCO-CH_3)_3 \cdot 2PPh_3$ in amounts of 0.001 to 1, specifically 0.005 to 0.25 mole per mole of dialkyl carbonate, as well as other lead(II) and lead (IV) compounds, such as PbO, $PbO_2$, red lead, plumbites and plumbates, iron(III) acetate, also copper salts and/or metal complexes, for example of alkali, zinc, titanium, and iron.

It is further possible to use heterogeneous catalyst systems. Such systems are, for example, mixed oxides of silicon and titanium which are obtainable by common hydrolysis of silicon and titanium halides or titanium dioxides having a high BET surface area >20 meters squared per gram ($m^2/g$).

The catalyst, when homogeneous, can be introduced into the production column in dissolved or suspended form together with the stream containing the aromatic hydroxy compound. Alternatively, the catalyst can also be metered in separately, for example in the reaction alcohol or a suitable inert solvent. A heterogeneous catalyst can be used in a packed bed, a column, or in special catalytic distillation arrangements, as well as in other arrangements.

Method of Making

Figure 1:
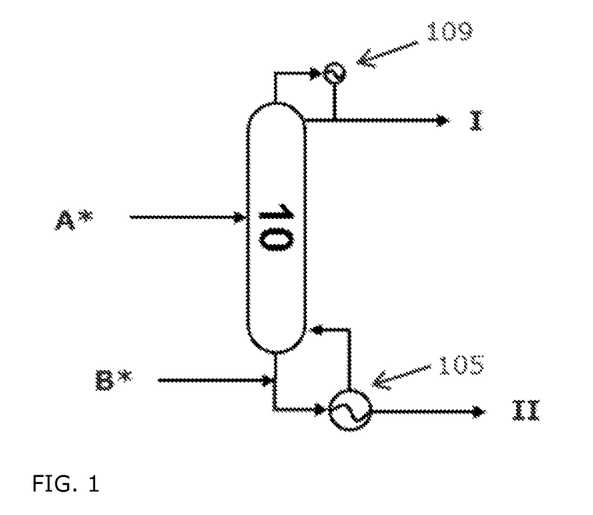
FIG. 1 is a schematic representation of an example of an alkyl aryl carbonate/diaryl carbonate production column.

FIG. 1 illustrates a typical production column for the preparation of product alkyl aryl carbonate (e.g., phenyl methyl carbonate)/diaryl carbonate G (e.g., diphenyl carbonate), where an aromatic hydroxy compound-rich stream A* comprising a homogeneous catalyst are introduced to a production column 10 comprising a condenser 109 and a reboiler 105, generally at a middle stage, while a dialkyl carbonate-rich stream B* comprising one or more of fresh dialkyl carbonate B, recycled dialkyl carbonate, and recycled aryl alkyl carbonate are generally introduced at a lower stage or even to the reboiler 105. Dialkyl carbonate can be fed in an excess amount to the production column 10, as dialkyl carbonate can serve as both a reactant and as a stripping agent, which facilitates the removal of, for example, methanol, in order to perform the transesterification reaction. In a continuous production process, a bottom stream II is continually removed from the bottom of the production column 10, where a portion of the bottom stream is heated in a reboiler using, for example, steam and a portion of the bottom stream is removed for further reaction and separation to ultimately obtain a purified diaryl carbonate. The bottom stream can comprise one or more of a diaryl carbonate, a catalyst, an alkyl aryl carbonate, an alkyl aryl ether, and an aromatic hydroxy compound. A top stream can also exit the production column, where the top stream can comprise one or more of a dialkyl carbonate, an aryl alkyl ether, and an alkyl alcohol.

Due to the large amount of vaporization involved, the production column 10 is the main thermal energy consumer in the whole diaryl carbonate production process, requiring for example, large amounts of steam for its operation.

The Applicants surprisingly found that they could employ a mechanical vapor recompression process on the overhead stream (e.g., overhead vapor stream) of the production column and use the heat from the overhead stream to heat the bottom stream of the production column. Specifically, the overhead vapor stream can be compressed until it condenses into a liquid, resulting in an increase in temperature of the stream. The latent of the condensed (overhead) stream can then be used to boil the bottom liquid in the reboiler 105. Likewise, the vapor recompression cycle can utilize the overhead vapor stream to heat an external liquid, where the external liquid is then used to heat the bottom stream that can comprise one or more of a diaryl carbonate, a catalyst, an alkyl aryl carbonate, and an aromatic hydroxy compound.

Specifically considering the production column, the column can be a distillation column, a reactive distillation column, a catalytic distillation column, or the like. The column can contain concentrating part(s) in the upper portion of the column and reaction zone(s) beneath the concentrating part, which can have at least two sections, wherein concentrating part(s) of the transesterification column can be equipped with intermediate condenser(s). Each of the sections, independently of the others, can have 5 or greater, specifically, 10 or greater theoretical equilibrium stages. At the top of the production column, the overhead vapor can be condensed in a condenser, wherein at least a portion of the condensed vapor can re-enter the production column. At the bottom of the production column, the bottom stream can be heated in a reboiler using the heat from the overhead vapors, wherein at least a portion of the heated bottom stream can re-enter the production column. The overhead vapor can comprise mainly dialkyl carbonate, an alkyl aryl ether, and alkyl alcohol.

Figure 2:
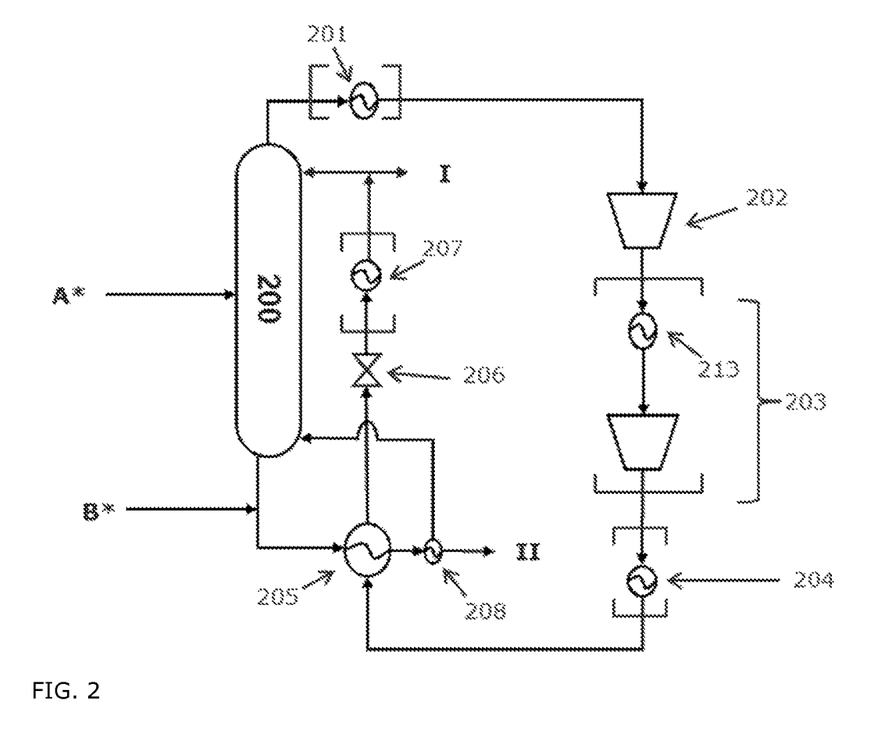
FIG. 2 is a schematic representation of an example of a production column employing a vapor recompression process using the overhead stream as the fluid.

FIG. 2 is an illustration of a vapor recompression process of a production column 200, where the temperature gradient is achieved by compressing the overhead vapor of the column so that it condenses at a higher temperature. The heat of condensation of this compressed stream is then used to heat the bottom stream of the column. Then, the pressure of this compressed and condensed stream is reduced using an expander device where after at least a portion can be returned back to the column as reflux.

Specifically, FIG. 2 illustrates that the overhead vapor can be heated in a super heater 201 to prevent condensation in the compressor 202. The compressed vapor from the compressor 202 can then be further compressed to form a finally compressed stream in a series of intermediate cooler and compressors 203, wherein the exact amount of coolers and compressors in the series 203 depends on the desired amount of compression and to further increase the temperature. Optionally, if the temperature is too high after passing through the series of coolers and compressors 203 the finally compressed stream can pass through a desuperheater 204 to reduce the temperature of the stream. The stream can then be optionally separated into its various components and/or separated into two or more substreams. The separation can occur before the reboiler 205 or in the reboiler 205. This separation can have the advantage of using less heat if the stream is separated.

The stream then passes through the reboiler 205, where the heat of condensation of the compressed stream is used to boil the bottom stream of the reboiler 205. After heating the bottom stream of the reboiler 205, the stream can be at least partially liquid and can then pass through an expansion valve 206 in order to reduce the pressure of the stream. If the stream is still too hot to be recycled back into the production column 200, the stream can first pass through a subcooler 207 to further reduce the temperature. The stream can then be split into a first stream and a second stream, wherein the first stream can be a reflux stream that enters to the top of the production column 200 and the second stream can be a distillate stream I.

In this manner, the bottom stream can be heated using the heat of condensation of the compressed vapor from the top of the production column 200. If the bottom stream is not sufficiently heated using this process, an extra reboiler 208 can be employed to ensure that the temperature of the bottom stream is heated to a minimum temperature of greater than or equal to the desired temperature, for example to a temperature of 180 to 260° C. Likewise, if the bottom stream is heated to a temperature greater than a maximum desired temperature, then an extra condenser can be employed to decrease the temperature.

Figure 3:
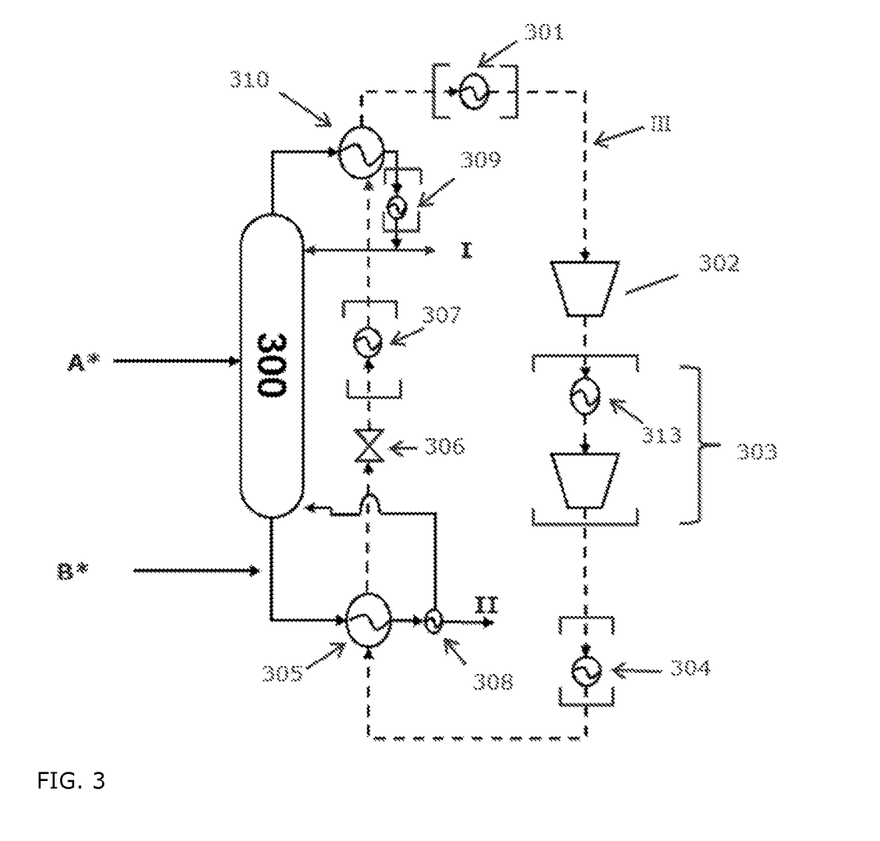
FIG. 3 is a schematic representation of an example of a production column employing a vapor recompression process using an external liquid as the fluid.

Alternatively, FIG. 3 illustrates a vapor recompression process around a production column 300 that relies on an external fluid working in a closed-loop. Here, the external fluid can be vaporized by condensing the overhead vapor of the column, recompressed, condensed by boiling the bottom liquid of the column, expanded and returned to the beginning of the cycle at its original pressure. The external fluid can be water, a $C_{4-30}$ hydrocarbon, a polyaromatic ether, or the like.

Specifically, FIG. 3 illustrates that the overhead vapor can be used to heat an external fluid III in the overhead condenser 310. The external fluid III can then pass through a superheater 301 to prevent condensation in the compressor 302. The compressed external fluid III from the compressor 302 can then be further compressed to form a finally compressed external fluid III in a series of coolers and compressors 303, wherein the exact amount of coolers and compressors in the series 303 can depend on the desired amount of compression and to further increase the temperature. Optionally, if the temperature is too high after passing through the series of superheaters and compressors 303 the finally compressed stream can pass through a desuperheater 304 to reduce the temperature of the external fluid III.

The external fluid III can then pass through the reboiler 305, where the heat of condensation of the compressed external fluid III is used to boil the bottom stream of the reboiler 305. After heating the bottom stream of the reboiler 305, the external fluid III can be at least partially liquid and can then pass through an expansion valve 306 in order to reduce the pressure of the stream. If the external fluid III is too hot, the external fluid III can pass through a subcooler 307 to further reduce the temperature.

In this manner, the bottom stream can be heated using the heat of condensation of the compressed vapor from the top of the production column 300. If the bottom stream is not sufficiently heated using this process, an extra reboiler 308 can be employed to ensure that the temperature of the bottom stream is heated to a minimum temperature of greater than or equal to the desired temperature, for example to a temperature of 180 to 260° C. Likewise, if the bottom stream is heated to a temperature greater than a maximum temperature, then an extra condenser can be employed to decrease the temperature.

In the illustrations of both FIGS. 2 and 3, a top stream I and a bottom stream II can exit the production column, where the top stream I can comprise a dialkyl carbonate, an aryl alkyl ether and an alkyl alcohol and the bottom stream II can comprise an aryl alkyl carbonate, an aromatic hydroxy compound, a diaryl carbonate, and a catalyst.

The exact design of the vapor recompression process can depend on how a temperature driving force is created to force heat to flow from the cooler overhead vapor to the hotter bottom product liquid. As it is schematically shown between brackets in FIGS. 2 and 3, the condenser and reboiler duties might not match, requiring an extra supply of cooling or heating capacity in addition to the work supplied to the compressors. This installation may incorporate one or more compressors and auxiliary equipment such as superheaters at the inlet to the compressor, desuperheaters at compressor outlet, intercoolers between different compression stages and/or subcoolers at expander outlet. Furthermore, compressors cannot generally tolerate liquid droplets and so, super-heaters for vaporizing wet vapor and/or knock-out drums for separating any liquid particles can also be used.

It is noted that while exemplary embodiments refer to using the vapor from the top stage(s) of the distillation column, one skilled in the art readily understands that the description of vapor recompression can be extended to cover any vapor taken from an intermediate stage of the column that is condensed in an inter-condenser and used to boil-up the liquid from an intermediate stage below in an inter-reboiler.

In an embodiment, a process for preparing an alkyl aryl carbonate and a diaryl carbonate, comprising: reacting a dialkyl carbonate and an aromatic hydroxy compound in a production column 200,300 to form the alkyl aryl carbonate and the diaryl carbonate; directing a bottom stream of the production column to a reboiler 205,305, wherein the bottom stream comprises the alkyl aryl carbonate and the diaryl carbonate; heating the bottom stream in the reboiler 205,305 with heat from an overhead stream of the production column 200,300 to result in a heated bottom stream; directing a first portion of the heated bottom stream back into the production column 200,300, wherein the first portion comprises an aromatic hydroxy compound; and collecting the diaryl carbonate and the alkyl aryl carbonate from a second portion of the heated bottom stream.

In another embodiment, a process for preparing an alkyl aryl carbonate and a diaryl carbonate can comprise: reacting a dialkyl carbonate and an aromatic hydroxy compound in a production column 200 to form the alkyl aryl carbonate and the diaryl carbonate; compressing an overhead stream in a compressor 203 resulting in a heated overhead stream; directing a bottom stream of the production column 200 and at least a portion of the heated overhead stream into a reboiler 205; heating the bottom stream in the reboiler 205 with heat from the heated overhead stream, resulting in a cooled overhead stream; directing at least a portion of the cooled overhead stream back into the production column 200; directing a first portion of the heated bottom stream back into the production column 200, wherein the first portion comprises an aromatic hydroxy compound; and collecting the diaryl carbonate and the alkyl aryl carbonate from a second portion of the heated bottom stream.

In an embodiment, a process for preparing an alkyl aryl carbonate and a diaryl carbonate, comprising: reacting a dialkyl carbonate and an aromatic hydroxy compound in a production column 200, 300 to form the alkyl aryl carbonate and the diaryl carbonate; directing a bottom stream of the production column to a reboiler 205, 305, wherein the bottom stream comprises the alkyl aryl carbonate and the diaryl carbonate; heating the bottom stream in the reboiler 205, 305 with heat from an overhead stream of the production column 200, 300 to result in a heated bottom stream; directing a first portion of the heated bottom stream back into the production column 200, 300, wherein the first portion comprises phenol; and collecting the diaryl carbonate and the alkyl aryl carbonate from a second portion of the heated bottom stream.

In another embodiment, a process for preparing an alkyl aryl carbonate and a diaryl carbonate can comprise: reacting a dialkyl carbonate and an aromatic hydroxy compound in a production column 200 to form the alkyl aryl carbonate and the diaryl carbonate; compressing an overhead stream in a compressor 203 resulting in a heated overhead stream; directing a bottom stream of the production column 200 and at least a portion of the heated overhead stream into a reboiler 205; heating the bottom stream in the reboiler 205 with heat from the heated overhead stream, resulting in a cooled overhead stream; directing at least a portion of the cooled overhead stream back into the production column 200; directing a first portion of the heated bottom stream back into the production column 200, wherein the first portion comprises phenol; and collecting the diaryl carbonate and the alkyl aryl carbonate from a second portion of the heated bottom stream.

In another embodiment, a process for preparing alkyl aryl carbonate and diaryl carbonate can comprise: reacting a dialkyl carbonate and an aromatic hydroxy compound in a production column 300 to form the alkyl aryl carbonate and the diaryl carbonate, wherein the production column 300 has an overhead stream and a bottom stream; heating an external fluid III with heat from the overhead stream in a condenser 310; compressing the external fluid III in a compressor 303 resulting in a heated external fluid III; heating the bottom stream with the heated external fluid III in the reboiler 305 to result in a heated bottom stream and a cooled external fluid III; directing a first portion of the heated bottom stream back into the production column 300; collecting the diaryl carbonate and the alkyl aryl carbonate from a second portion of the heated bottom stream; and directing the cooled external fluid III back into the condenser 310 such that the external fluid III flows in a closed loop.

In yet another embodiment, a process for preparing alkyl aryl carbonate and diaryl carbonate can comprise: reacting a dialkyl carbonate and an aromatic hydroxy compound in a production column 300 to form the alkyl aryl carbonate and the diaryl carbonate, wherein the production column 300 has an overhead stream and a bottom stream; heating an external fluid III with heat from the overhead stream in a condenser 310; compressing the external fluid III in a compressor 303 resulting in a heated external fluid III; heating the bottom stream with the heated external fluid III in the reboiler 305 to result in a heated bottom stream and a cooled external fluid III; directing a first portion of the heated bottom stream back into the production column 300; collecting the diaryl carbonate and the alkyl aryl carbonate from a second portion of the heated bottom stream; and directing the cooled external fluid III back into the condenser 310 such that the external fluid III flows in a closed loop. The diaryl carbonate comprises at least one of diphenyl carbonate, diethyl carbonate, and dibutyl carbonate; the dialkyl carbonate comprises at least one of dimethyl carbonate, dipropyl carbonate, dibutyl carbonate, and diethyl carbonate; the alkyl aryl carbonate comprises at least one of phenyl methyl carbonate, phenyl ethyl carbonate, propyl phenyl carbonate, and butyl phenyl carbonate; and an aromatic hydroxy compound comprises phenol. Optionally, the aromatic hydroxy compound can comprise at least one of cresols, ethyl phenols, propyl phenols, and butyl phenols.

In the various embodiments: (i) the heating of the bottom stream comprises compressing the overhead stream in a compressor 203 resulting in a heated overhead stream, and heating the bottom stream with the heated overhead stream; and/or (ii) further comprising splitting the heated overhead stream after it passes through the reboiler 205 into a reflux stream that re-enters the production column 200 and a distillate stream I; and/or (iii) the heating of the bottom stream involves heating an external fluid III with the overhead stream in a condenser 310, compressing the external fluid III in a compressor 303, and heating the bottom stream in the reboiler 305 with the compressed external fluid III, wherein the external fluid III flows in a closed loop; and/or (iv) a supply of thermal capacity in addition to the energy supplied to the compressor; and/or (v) further comprise a compressor 202, 302; and/or (vi) further comprise an auxiliary equipment at an inlet and/or an outlet to the compressor, wherein the auxiliary equipment comprises one or more of a desuperheater 204, 304, an intercooler between two compressors 213, 313, a subcooler at an outlet of an expansion valve 206, 306, superheater 201, 301, and knock-out drums for separating any liquid particles; and/or (vii) the diaryl carbonate comprises diphenyl carbonate, the dialkyl carbonate comprises at least one of dimethyl carbonate, dipropyl carbonate, dibutyl carbonate, and diethyl carbonate, the alkyl aryl carbonate comprises at least one of phenyl methyl carbonate, phenyl ethyl carbonate, propyl phenyl carbonate, and butyl phenyl carbonate, and an aromatic hydroxy compound comprises phenol; and/or (viii) the aromatic hydroxy compound comprises at least one of cresols, ethyl phenols, propyl phenols, and butyl phenols; and/or (ix) a temperature difference between the condenser 210, 310 and the reboiler 205, 305 is greater than or equal to 10° C.; and/or (x) a temperature difference between the condenser 210, 310 and the reboiler 205, 305 is greater than or equal to 20° C.; and/or (xi) the diaryl carbonate comprises diphenyl carbonate, the dialkyl carbonate comprises dimethyl carbonate, the alkyl aryl carbonate comprises phenyl methyl carbonate, and an aromatic hydroxy compound comprises phenol; and/or (xii) the diaryl carbonate is diethyl carbonate; and/or (xiii) the diaryl carbonate comprises dibutyl carbonate; and/or (xiv) the diaryl carbonate is diphenyl carbonate.

The following examples are provided to illustrate the vapor recompression process. The examples are merely illustrative and are not intended to limit devices made in accordance with the disclosure to the materials, conditions, or process parameters set forth therein.

EXAMPLES

Comparative Example 1

50,840 kilogram per hour (kg/h) of a phenol-rich stream (80.5 wt %) PhOH, 10.4 wt % DMC, 4.7 wt % anisole (ANS), 2.8 wt % titanium tetraphenoxide catalyst, 0.9 wt % DPC and 0.7 wt % high boilers (HBs; i.e., moieties with a boiling point greater than DPC, such as 2-methoxyphenyl benzoate, xanthone, and others)) was fed at a middle height of a reactive PMC/DPC distillation production column 10 in FIG. 1. 117,000 kg/h of a DMC-rich stream B (97.1 wt % DMC, 2.7 wt % anisole, 0.1 wt % MeOH) was directly fed to the reboiler of this column. Temperature and pressure profiles ranged from 210° C. and 5.6 bar at the reboiler 105 to 130° C. and 5.2 bar at the condenser 109 of the column. The distillate rate was 98,090 kg/h (93.8 wt % DMC, 4.2 wt % MeOH, 1.9 wt % anisole) while the reflux ratio of the column was 0.86. The bottom product rate was 69,750 kg/h (41.7 wt % PhOH, 25.0 wt % PMC, 23.0 wt % DMC, 2.5 wt % DPC, 5.2 wt % anisole, 2.0 wt % catalyst, and 0.5 wt % HBs) while the boil-up ratio was 2.9. This column had a heating requirement of 20,079 kilowatt (kW) as steam in the reboiler while the condenser removes a duty of 18,598 kW.

Example 2

The PMC/DPC production distillation column described in Comparative Example 1 was used in Example 2, where the vapor recompression cycle around production column 200 was used in place of column 10 from the comparative example. The internal streams, product distillate, reflux rate, and residue stream conditions, flowrates, and compositions in this example were the same as those of Comparative Example 1. The vapor stream from the last stage of the distillation column was superheated in superheater 201 to 165° C. and then compressed in compressor 202 and 203 to 24 bar in a series of two compressors (total power=4,160 kW, adiabatic efficiency 75%). At the resulting conditions (24.0 bar, 238° C.), this stream was completely condensed by exchanging −12,877 kW in the reboiler 205 of the production column 200. The heat released from this condensation was used in the reboiler 205 of the column, while the rest of the heating duty (20,079 kW-12,877 kW=7,202 kW) required for vaporizing all the boil-up rate was supplied in an extra reboiler 208 by extra high-pressure steam. Liquid condensate at 24.0 bar and 221° C. was passed through an expansion valve 206 and totally condensed in a subcooler 207 in order to prepare this stream at the conditions of 5.2 bar and 130° C. The resulting liquid was split as the distillate and the reflux for the column.

Table 1 shows a detailed comparison between the heating and cooling requirements for the column stand-alone (Comparative Example 1) and the column using this vapor recompression cycle.

TABLE 1

|  | CE 1 | 2 | Difference |
|---|---|---|---|
| Reboiler 105, 205 duty, kW | 20079 | 7202* |  |
| Superheater 201 duty, kW | — | 2029 |  |
|  |  |  |  |
| Total heating duty, kW | 20079 | 9231 | −10848 (−54.0%) |
| First compressor, kW | — | 2276 |  |
| Second compressor, kW | — | 1884 |  |
| Compressor 202 power, kW | — | 4160 | +4160 |
| Condenser 109, 207 duty, kW | 18598 | −11955+ |  |
| Cooling duty, kW | 18598 | 11955 | −6643 (−35.7%) |

*Extra reboiler,
+Subcooler 207

Table 1 shows that the vapor recompression process achieves a reduction of 54.0% and 35.7% in the heating and cooling requirements, respectively. The compression power for this example was 4,160 kW.

Example 3

The PMC/DPC production distillation column described in Comparative Example 1 was used in Example 3, where the vapor recompression cycle around production column 300 was used in place of production column 10 from the comparative example. The internal streams, product distillate, reflux rate, and residue stream conditions, flowrates, and compositions in this example were the same as those of Comparative Example 1. 34,230 kg/h of saturated water vapor at 120° C. and 2 bar were compressed in a series of 3 compressors 302 and 303 (total power=5,422, adiabatic efficiency 75%) with two intermediate intercoolers 313 with total cooling duties of 1,126 and 1,370 kW to 342° C. and 28 bar. This superheated steam was used as the heating medium to supply 15,185 kW in the reboiler 305 of the PMC/DPC production column by condensation. The resulting saturated water liquid at 230° C. passed through an expansion valve 306 reducing its pressure and reaching saturated liquid conditions (120° C. and 2 bar). This liquid water was then vaporized, so acting as the cooling medium (16,740 kW) in the condenser 310 of the column and closing the loop. Some extra cooling duty (18, 598−16870=1,728 kW) was required in an additional condenser, subcooler 307 in order to supply all the cooling requirements for the total condensation of the column overhead vapor.

Table 2 presents a comparison between the energy requirements of the PMC/DPC production column stand-alone (Comparative Example 1) and the same column with the vapor recompression cycle described in Example 3.

TABLE 2

|  | 1 | 3 | Difference |
|---|---|---|---|
| Reboiler 105 duty, kW | 20079 | — |  |
| Superheater duty, kW | — | — |  |
|  |  |  |  |
| Total heating duty, kW | 20079 | — | −20079 |
| First compressor, kW | — | 1798 |  |
| Second compressor, kW | — | 2155 |  |
| Third compressor, kW | — | 2491 |  |
| Compressor 302 + 303 power, kW | — | 6444 | +6444 |
| Condenser 109, 309 duty, kW | 18598 | 1728 |  |
| Intercooler 313 duty, kW | — | 1453 |  |
| Intercooler 313 duty, kW | — | 1778 |  |
| Cooling duty, kW | 18598 | 4959 | −13396 (−73.3%) |

As Table 2 shows, heating duties can be completely avoided by using a series of 3 mechanical compressors of 1,798 kW, 2,155 kW, and 2,491 kW with intermediate cooling. Therefore, no steam is consumed in this system while cooling requirements are reduced to 73.3% as compared to the column of Comparative Example 1.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt %, or, more specifically, 5 wt % to 20 wt %", is inclusive of the endpoints and all intermediate values of the ranges of "5 wt % to 25 wt %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements can be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

We claim:

1. A process for preparing an alkyl aryl carbonate and a diaryl carbonate, comprising:
reacting a dialkyl carbonate and an aromatic hydroxy compound in a production column to form the alkyl aryl carbonate and the diaryl carbonate;
directing a bottom stream of the production column to a reboiler, wherein the bottom stream comprises the alkyl aryl carbonate and the diaryl carbonate;
heating the bottom stream in the reboiler with heat from an overhead stream of the production column to result in a heated bottom stream;
directing a first portion of the heated bottom stream back into the production column, wherein the first portion comprises the aromatic hydroxy compound; and
collecting the diaryl carbonate and the alkyl aryl carbonate from a second portion of the heated bottom stream.

2. The process of claim 1, wherein the heating of the bottom stream comprises
compressing the overhead stream in a compressor resulting in a heated overhead stream; and
heating the bottom stream with the heated overhead stream.

3. The process of claim 2, further comprising splitting the heated overhead stream after it passes through the reboiler into a reflux stream that re-enters the production column and a distillate stream I.

4. The process of claim 1, wherein the heating comprises
heating an external fluid III with the overhead stream in a condenser;
compressing the external fluid III in a compressor; and
heating the bottom stream in the reboiler with the compressed external fluid III;
wherein the external fluid III flows in a closed loop.

5. The process of claim 2, further comprising a supply of thermal capacity in addition to an energy supplied to the compressor.

6. The process of claim 1, further comprising a compressor.

7. The process of claim 6, further comprising an auxiliary equipment at an inlet and/or an outlet to the compressor, wherein the auxiliary equipment comprises one or more of a desuperheater, an intercooler between the compressor and a second compressor, a subcooler at an outlet of an expansion valve, superheater, and knock-out drums for separating any liquid particles.

8. The process of claim 1, wherein
the diaryl carbonate comprises diphenyl carbonate;
the dialkyl carbonate comprises at least one of dimethyl carbonate, dipropyl carbonate, dibutyl carbonate, and diethyl carbonate;
the alkyl aryl carbonate comprises at least one of phenyl methyl carbonate, phenyl ethyl carbonate, propyl phenyl carbonate, and butyl phenyl carbonate; and
an aromatic hydroxy compound comprises phenol.

9. The process of claim 1, wherein the aromatic hydroxy compound comprises at least one of cresols, ethyl phenols, propyl phenols, and butyl phenols.

10. The process of claim 1, wherein the production column comprises a condenser, wherein a temperature difference between the condenser and the reboiler is greater than or equal to 10° C.

11. The process of claim 1, wherein the production column comprises a condenser, wherein a temperature difference between the condenser and the reboiler is greater than or equal to 20° C.

12. The process of claim 1, wherein the diaryl carbonate comprises diphenyl carbonate, the dialkyl carbonate comprises dimethyl carbonate, the alkyl aryl carbonate comprises phenyl methyl carbonate, and an aromatic hydroxy compound comprises phenol.

13. The process of claim 1, wherein the dialkyl carbonate is diethyl carbonate.

14. The process of claim 1, wherein the dialkyl carbonate comprises dibutyl carbonate.

15. A process for preparing an alkyl aryl carbonate and a diaryl carbonate comprises:
reacting a dialkyl carbonate and an aromatic hydroxy compound in a production column to form the alkyl aryl carbonate and the diaryl carbonate;
compressing an overhead stream in a compressor resulting in a heated overhead stream; directing a bottom stream of the production column and at least a portion of the heated overhead stream into a reboiler;
heating the bottom stream in the reboiler with heat from the heated overhead stream, resulting in a cooled overhead stream;
directing at least a portion of the cooled overhead stream back into the production column;
directing a first portion of the heated bottom stream back into the production column, wherein the first portion comprises phenol; and
collecting the diaryl carbonate and the alkyl aryl carbonate from a second portion of the heated bottom stream.

16. A process for preparing alkyl aryl carbonate and diaryl carbonate comprises:
reacting a dialkyl carbonate and an aromatic hydroxy compound in a production column to form the alkyl aryl carbonate and the diaryl carbonate, wherein the production column has an overhead stream and a bottom stream;
heating an external fluid III with heat from the overhead stream in a condenser; compressing the external fluid III in a compressor resulting in a heated external fluid III;
heating the bottom stream with the heated external fluid III in the reboiler to result in a heated bottom stream and a cooled external fluid III;
directing a first portion of the heated bottom stream back into the production column;
collecting the diaryl carbonate and the alkyl aryl carbonate from a second portion of the heated bottom stream; and
directing the cooled external fluid III back into the condenser such that the external fluid III flows in a closed loop.

17. A process for preparing alkyl aryl carbonate and diaryl carbonate comprises:
reacting a dialkyl carbonate and an aromatic hydroxy compound in a production column to form the alkyl aryl carbonate and the diaryl carbonate, wherein the production column has an overhead stream and a bottom stream;
heating an external fluid III with heat from the overhead stream in a condenser;
compressing the external fluid III in a compressor resulting in a heated external fluid III;
heating the bottom stream with the heated external fluid III in the reboiler to result in a heated bottom stream and a cooled external fluid III;
directing a first portion of the heated bottom stream back into the production column;
collecting the diaryl carbonate and the alkyl aryl carbonate from a second portion of the heated bottom stream; and
directing the cooled external fluid III back into the condenser such that the external fluid III flows in a closed loop;

wherein the diaryl carbonate comprises diphenyl carbonate;
wherein the dialkyl carbonate comprises at least one of dimethyl carbonate, dipropyl carbonate, dibutyl carbonate, and diethyl carbonate;
wherein the alkyl aryl carbonate comprises at least one of phenyl methyl carbonate, phenyl ethyl carbonate, propyl phenyl carbonate, and butyl phenyl carbonate; and
wherein an aromatic hydroxy compound comprises phenol.

* * * * *